(12) United States Patent
Kanna et al.

(10) Patent No.: US 9,302,255 B2
(45) Date of Patent: Apr. 5, 2016

(54) OXIDATION CATALYST, THE PROCESS FOR THE PREPARATION THEREOF AND GREEN PROCESS FOR SELECTIVE AEROBIC OXIDATION

(71) Applicant: Council of Scientific & Industrial Research, New Delhi (IN)

(72) Inventors: Narasimharao Kanna, Pune (IN); Satyanarayana Vera Venkata Chilukuri, Pune (IN); Ganesh Dattatreya Kokate, Pune (IN); Lakshmiprasad Gurrala, Pune (IN)

(73) Assignee: Council Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/283,663

(22) Filed: May 21, 2014

(65) Prior Publication Data

US 2015/0336090 A1 Nov. 26, 2015

(51) Int. Cl.
*B01J 29/74* (2006.01)
*C01B 39/06* (2006.01)
*C07C 59/10* (2006.01)
*C01B 39/46* (2006.01)
*C07D 307/68* (2006.01)
*C07C 59/105* (2006.01)

(52) U.S. Cl.
CPC ............. *B01J 29/74* (2013.01); *C01B 39/06* (2013.01); *C01B 39/46* (2013.01); *C07C 59/10* (2013.01); *C07C 59/105* (2013.01); *C07D 307/68* (2013.01); *B01J 2229/183* (2013.01)

(58) Field of Classification Search
USPC ........................................................ 549/485
See application file for complete search history.

(56) References Cited

U.S. PATENT DOCUMENTS 5,523,509 A * 6/1996 O'Young ................. B01J 23/34
568/303

* cited by examiner

*Primary Examiner* — Kristin Vajda
(74) *Attorney, Agent, or Firm* — Fish & Richardson P.C.

(57) ABSTRACT

Described herein is a novel, cost effective, stable and recyclable catalyst composition i.e. A-B-OMS, wherein 'A' is selected from noble and transition metals; 'B' is selected from alkali or alkaline earth metals; and OMS is octahedral molecular sieve which includes synthetic todorokite (OMS-1) and cryptomelane (OMS-2); and characterization thereof. Further the invention provides base free green process for selective aerobic oxidation of 5-hydroxymethylfurfural (HMF) catalyzed by said catalyst composition under optimized reaction conditions to obtain high yield of 2,5-furandicarboxylic acid (FDCA) in a shorter span of time. Invention also provides for selective oxidation of glucose to Gluconic Acid, furfural to furoic Acid and glycerol to Glyceric acid. Invention can also applicable for the selective oxidation of hexoses, pentoses, disaccharides to corresponding acids.

13 Claims, 10 Drawing Sheets

(a) (b)

(a) (b)

OXIDATION CATALYST, THE PROCESS FOR THE PREPARATION THEREOF AND GREEN PROCESS FOR SELECTIVE AEROBIC OXIDATION

TECHNICAL FIELD OF THE INVENTION

The present invention provides novel oxidation catalyst, the process for the preparation thereof and green process for selective aerobic oxidation using said oxidation catalyst. The present invention relates to a novel, cost effective, stable and recyclable catalyst composition i.e. A-B-OMS, wherein 'A' is selected from noble metals; 'B' is selected from alkali or alkaline earth metals; and OMS is octahedral molecular sieve which includes synthetic todorokite (OMS-1) and cryptomelane (OMS-2); and characterization thereof. Particularly, the present invention provides a process for the preparation of catalyst composition A-B-OMS. More particularly, the invention provides base free green process for selective aerobic oxidation of 5-hydroxymethylfurfural (HMF), glucose, glycerol and furfural by said catalyst under optimized reaction conditions to obtain high yield of 2,5-furandicarboxylic acid (FDCA), Gluconic Acid, Glyceric acid and furoic Acid respectively in a shorter span of time.

BACKGROUND AND PRIOR ART

Efficient utilization of biomass for the sustainable production of chemicals and energy is an important way to reduce dependence on fossil resources, which helps in the containment of $CO_2$ emissions. Hence, researchers are focusing on technologies that can facilitate the conversion of renewable biomass into fuels and chemicals. Moreover, future economic and industrial growth of a nation depends upon its ability to utilize locally available sustainable feedstock (biomass) for fuel and chemical production. Hence, there is a need to shift from traditional petrochemical feedstock towards biomass based feedstock that preserves ecology as well as leads to economic gains of a nation (C. H. Christensen et al., *ChemSusChem* 2008, 1, 283)

HMF is a biomass/cellulose derived component, obtained without fermentation, thus it is a potential "carbon-neutral" feedstock for fuels and chemicals. HMF on selective oxidation gives corresponding dicarboxylic acid, wherein HMFCA (5-hydroxymethyl-2-furancarboxylic acid) is formed on oxidation of HMF, which is gradually converted to FDCA, a more stable product.

Bearing in mind the utilisation of biomass as a primary substrate, several sustainable feedstocks have been suggested. Hexoses are abundant monosaccharides existing in nature. Selective dehydration of hexoses gives a potential platform chemical called 5-hydroxymethylfurfural (HMF). Under specific reaction conditions, HMF can be oxidized to yield 2,5-furandicarboxylic acid (FDCA), which is a valuable chemical intermediate. US DOE biomass program has identified FDCA as one of the 12 important chemicals derived from biomass that can be used as a chemical building block in future. It is a potential replacement source of terephthalic acid; the monomer is currently used for the production of polyethylene terephthalate (PET) and derived from hydrocarbon sources.

A number of different homogeneous and heterogeneous catalyst systems have previously been reported for the selective oxidation of HMF to FDCA. Use of stoichiometric oxidant $KMnO_4$ and industrially practiced catalyst Co/Mn/Br were also reported. Direct synthesis from fructose has been attempted using a solid acid and Pt/Bi/C in water/Methyl isobutene Ketone, yielding 25% FDCA with 50% selectivity.

Furthermore Ribeiro et. al, obtained 71% yield of FDCA using silica-encapsulated cobalt acetylacetonate as a bifunctional acid-redox catalyst at 160° C. (*Catal. Commun.* 2003, 4, 83)

Lilga et al. have reported an industrially promising method to oxidize HMF to FDCA in up to 98% yield at 100° C. and 1 MPa oxygen pressure using a $Pt/ZrO_2$ catalyst (US Patent 20080103318, 2008). Gorbanev et al. demonstrated that $Au/TiO_2$ could oxidize HMF into FDCA in 71% yield at room temperature (*ChemSusChem* 2009, 2, 672). Corma and co-workers have showed that $Au/CeO_2$ was found to be more selective for FDCA (*ChemSusChem*, 2009, 2, 113). Pasini et al. obtained high yield of FDCA from HMF using supported Au—Cu nano particles as catalyst (*Green Chem* 2011, 13, 2091). Villa et al. showed that Pd-modified Au on Carbon as an effective catalyst for the FDCA production from HMF (*ChemSusChem* 2013, 6, 60). Oxidation of 5-hydroxymethylfurfural over supported Pt, Pd and Au catalysts such as Pt/C, Pd/C Au/C and $Au/TiO_2$ reported.

Although some of the above reported processes produce high yields of FDCA, usage of homogeneous base (1-20 equiv. NaOH) and high oxygen pressure (10-20 bar) makes them difficult to scale up. In order to make the process free of corrosive base, researchers have conducted the above reaction without base. Gupta et al. have reported hydrotalcite-supported gold-nanoparticles as a base free catalyst for HMF oxidation which produce 99% yield of FDCA (*Green Chem.*, 2011, 13, 824). Recyclability of the above catalyst is an issue due to the Leaching of $OH^-$ and $HCO_3^-$ groups after reaction from the support. Riisager and his co-workers have worked over spinel supported Ru catalyst, but the yield of FDCA was not good enough for scale up (*Top Catal* (2011) 54, 1318). Aerobic oxidation of HMF to FDCA with ruthenium containing ferrite-spinel catalyst is demonstrated by Ester Eyjolfsdottir et al. However, the process is time consuming to get good yield of FDCA.

U.S. Pat. No. 5,523,509 and U.S. Pat. No. 5,702,674 (Oyoung, Chi-lin et al.) described OMS-1 tunnel-substituted with a metal cation selected from the group consisting of Li, Na, K, Cs, Mg, Ca, Ba, Co, Ni, Cu and Zn. Selective oxidation of alcohols using octahedral molecular sieves was demonstrated by Young-Chan Son et al., in U.S. Pat. No. 6,486,357.

Manganese oxides with tunnel structures exhibiting molecular sieving properties are referred to as manganese oxide octahedral molecular sieves (OMS). They include synthetic todorokite (OMS-1) and cryptomelane (OMS-2). Manganese oxide octahedra ($MnO_6$) are the basic structural units of OMS materials that combine to form tunnels by linkages at their edges and vertexes. OMS-1 utilizes three $MnO_6$ octahedra on each side to form a 3×3 square tunnel with a pore size of about 6.9 Å. Similarly, OMS-2 has a 2×2 square tunnels with pore size of about 4.6 Å. Inside the tunnel of these OMS structures, K (cryptomelane) or Mg (todorokite) ions are present as exchangeable cations. Hui Huang et al., describes a facile single-step method developed for synthesizing todorokite-type manganese oxide octahedral molecular sieves (OMS-1) (*Chem. Commun.*, 2010, 46, 5945).

In view of above prior art, metal catalysts employed in the synthesis of FDCA accompany technical constrains such as lack of recyclability due to Leaching of metal support, time consuming process, poor yield of the product, necessity of base, industrial feasibility. This creates the need of alternative stable, cost-effective and recyclable catalyst which obviates requirement of base to produce high yield of FDCA in short period of time.

There are only a few reports on the selective oxidation of HMF to FDCA in the absence of base. Even in case of reported catalysts that have both basic component and redox center, they lack recyclability. Leaching of the basic active center makes the process difficult to recycle.

To overcome the short comings of the prior art, the present inventors have developed alternative, cost-effective, recyclable catalyst composition comprising metal loaded or exchanged alkali or alkaline earth metal oxide octahedral molecular sieves; having both redox and basic sites, as the basic sites are part of the structure and does not leach out during the reaction and also obtained in very good yields of FDCA within short span of reaction time. Further the said catalyst is highly active for selective oxidation of HMF to obtain FDCA in high yield and selectivity in short reaction time.

Gluconic acid (GA) is a mild organic acid which is an important chelating agent with many applications in the chemical industry. Major part of its production is used in food industry. It is also used in pulp and paper manufacturing, water treatment and in the pharmaceutical industry. Around the globe, it is produced to the tune of 100,000 tonne per annum. Gluconic acid can be manufactured in different ways, viz., chemical, electrochemical, biochemical and bioelectrochemical. But, majority of its production is carried out through fermentation process in which enzymes like *Aspergillus niger* and *Gluconobacter suboxydons* oxidizes glucose. The main obstacle to the large-scale application of the fermentation processes is that it requires neutralization of the acid in order to avoid deactivation of the enzymes.

Scheme-1. Reaction scheme of glucose oxidation to gluconic acid

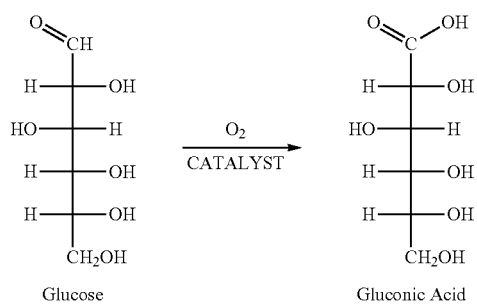

Oxidation of glucose to gluconic acid over noble metal catalysts, including Pt, Pd and Au, has been reported extensively. Gold catalysts show superior activity and selectivity to gluconic acid when compared to other precious metals such as Pd or Pt. Baatz et al. attributed superior performance of Au to its resistivity to poisoning and overoxidation (*J. Catal.*, 2002, 206, 242-247). Biella and co-workers used Au supported on activated carbon in the pH range of 7.0 to 9.5 for glucose oxidation. They found that Au particles tend to agglomerate after the reaction. If metal oxides ($Al_2O_3$, $TiO_2$) are used as support, Au can resist sintering and agglomeration compared to the carbon supports.

Recently Leshkov's group reported base free oxidation of glucose to gluconic acid using $CeO_2$ as support. but, most of the reports suggest that this reaction is best conducted by adding an external base to maintain pH in 7.5-12 range. Since, most of the work was conducted using acidic or neutral catalyst supports, it was necessary to add an external base. It is well known that gold particles tend to sinter at high pH during the reaction. Hence, it is recommended that the reaction is best conducted in the absence of a base. We have carried out oxidation of glucose using precious metal supported on a microporous material with basic properties. Since, the alkaline earth metal in the support has basic property; it can donate electrons to Au to keep it in reduced state, leading to stable activity of the catalyst.

2-Furoic acid (FA) is an important intermediate, which is mainly obtained by oxidation of furfural. It is widely used as a preservative and flavouring agent. It is also used as a non linear optical material and also in the preparation of nylon. Commercial production of FA is conducted through microbial route using organism called *Nocardia coralline*.

Oxidation of furfural to FA was studied with different homogeneous catalysts, $MnO_2$, $KMnO_4$ and NaOCl. since these processes use stoichiometric quantities of these reagents; their disposal is an environmental issue. Heterogeneous catalysts like $Ag_2O$ mixture of metallic oxides like Cu, Fe were also reported for the oxidation of furfural. Verdeguer et. al. used lead/platinum on charcoal as catalyst for the above reaction. In all these processes, base is used as promoter (*Applied Catalysis A: General*, 1994, 112). Disposal of base is tedious and there are environmental issues associated with it. Till today, there were no reports on base free process for the above reaction. However, we have conducted furfural oxidation without addition of external base.

OBJECTIVE OF THE INVENTION

The main objective of the present invention is to provide novel oxidation catalyst the process for the preparation thereof and green process for selective aerobic oxidation using said oxidation catalyst.

Another objective of the present invention is to provide a novel, cost effective, stable and recyclable catalyst composition i.e. A-B-OMS, wherein 'A' is selected from noble metals; 'B' is selected from alkali or alkaline earth metals; and OMS is octahedral molecular sieve which includes synthetic todorokite (OMS-1) and cryptomelane (OMS-2); and characterization thereof.

Another objective of the present invention is to provide a process for the preparation of catalyst composition A-B-OMS.

Still another objective of the present invention is to provide base free green process for selective aerobic oxidation of 5-hydroxymethylfurfural (HMF), glucose, glycerol and furfural by said catalyst under optimized reaction conditions to obtain high yield of 2,5-furandicarboxylic acid (FDCA), Gluconic Acid, Glyceric acid and furoic Acid respectively in a shorter span of time.

SUMMARY OF THE INVENTION

Accordingly, the present process relates to a selective oxidation catalyst having general formula A-B-OMS, wherein A is a metal selected from the group consisting of Ru, Au, Pt, Pd, Rh, OS, Ni, Co or Cu either alone or combination in the range of 0.1-5 wt % of catalyst; B is selected from K, Na, Li, Rb, Cs or Mg, Ca, Sr, Ba either alone or combination thereof in the range of 0.1-10 wt % of catalyst; and OMS is octahedral molecular sieve selected from the group consisting of synthetic todorokite (OMS-1) and K-cryptomelane (OMS-2).

In an embodiment of the present invention the catalyst is selected from the group consisting of Ru—Mg-OMS1, Ru—Mg-OMS2, Ru—Mg—K-OMS1 Ru—Mg—K-OMS2, Au—Mg-OMS1, Pt—Mg-OMS1, Pd—Mg-OMS1 and Au—Pt—Mg-OMS1.

In one embodiment of the present invention a process for the preparation of catalyst having general formula A-B-OMS according to claim 1, comprising steps of;
  a) ion-exchanging of sodium-buserite with metal (B) salts by stirring at temperature ranging between 25-35° C. for a period ranging between 12-36 hrs followed by adding solution of metal (B) salts into it and heating at temperature ranging between 120 to 160° C. for a period ranging between 24-48 hrs to obtain B-OMS;
  b) stirring B-OMs as obtained in step (a) with A-metal salts at temperature ranging 60 to 100° C. for 2 to 4 h and after cooling adding a reducing agent selected from $NaBH_4$ or $LiAlH_4$ into it and stirring at temperature ranging between 30-40° C. for a period ranging between 1-3 hrs to obtain A-B-OMs.

In another embodiment of the present invention the metal (B) salt used in step (a) is selected from the group consisting of NaCl, KCl, $MgCl_2$, LiCl, $CaCl_2$, $Mg(NO3)_2$; preferably $MgCl_2$.

In another embodiment of the present invention the (A) metal salts used in step (b) is selected from the group consisting of $RuCl_3$, $PtCl_2$, $RhCl_3$, $OsCl_3$, $CuCl_2$, $PdCl_2$, $AuCl_3$.

Still in another embodiment of the present invention a base free green process for selective oxidation in presence of catalyst (A-B-OMS) as claimed in claim 1, wherein the said process comprises charging a reactant in the range of 0.5 to 5 mmol, water and A-B-OMS catalyst in a reactor and heating the reactor while stirring at speed ranging between 500-1000 rpm to reach temperature ranging between 90-120° C. subsequently after reaching the temperature, sending oxygen into the reactor at pressure ranging between 1-3 bar to obtain oxidized product.

Still in another embodiment of the present invention reactant used is selected from the group consisting of 5-hydroxymethylfurfural (HMF), Glucose, Glycerol and Furfural.

Still in another embodiment of the present invention oxidized product obtained is selected from the group consisting of 2,5-furandicarboxylic acid (FDCA), Gluconic Acid, Glyceric acid and 2-Furoic Acid.

Still in another embodiment of the present invention the A-B-OMS catalyst is selected from the group consisting of Ru—Mg-OMS1, Ru—Mg-OMS2, Ru—Mg—K-OMS1 Ru—Mg—K-OMS2, Au—Mg-OMS1, Pt—Mg-OMS1, Pd—Mg-OMS1 and Au—Pt—Mg-OMS1.

Still in another embodiment of the present invention ratio of reactant to catalyst ranging between 50-500.

Still in another embodiment of the present invention the oxidation is completed within 4-6 h.

Still in another embodiment of the present invention yield of oxidised product is in the range of −10-95%.

BRIEF DESCRIPTION OF FIGURES

FIG. (1) depicts XRD pattern of (a) Na-Buserite (b) Mg-Buserite (c) Mg-OMS-1, (d) 2 wt % Ru—Mg-OMS-1, FIG. (2) depicts TGA profile of Mg-OMS-1 in $N_2$, FIG. (3) depicts SEM image of (a) Mg-OMS-1, (b) 2 wt % Ru—Mg-OMS-1, FIG. (4) depicts TEM image of (a) Mg-OMS-1, (b) 2 wt % Ru—Mg-OMS-1, FIG. (5) depicts $CO_2$-TPD profile of Mg-OMS-1 catalyst, FIG. (6) depicts Effect of time and temp on the Yield of FDCA, Conditions: 1.3 mmol HMF, 20 ml water 2% Ru-mg-OMS-1=80 mg, 2 bar $O_2$.

FIG. (7) depicts effect of catalyst content on the Yield of FDCA, Conditions: 1.3 mmol HMF, 20 mL water, 2% Ru—Mg-OMS, Pressure=2 bar $O_2$.

Figure 1:
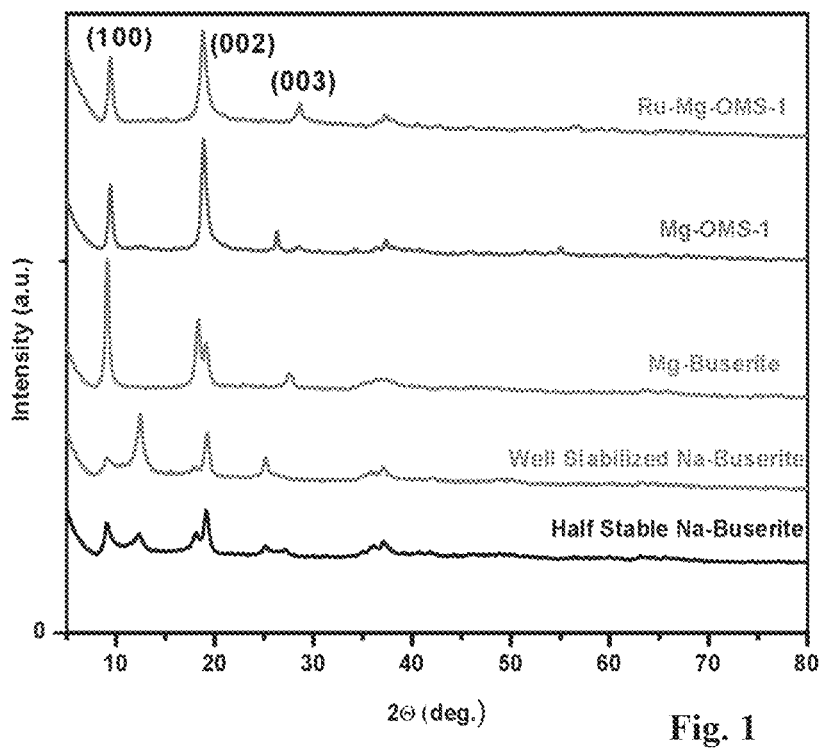

FIG. (8) depicts effect of oxygen pressure on the Yield of FDCA, Conditions: 1.3 mmol HMF, 20 mL water, 2 wt % Ru—Mg-OMS-1=80 mg, temp=100° C., FIG. (9) depicts effect of metal loading on the Yield of FDCA Conditions: 1.3 mmol HMF, 20 mL water, Cata=80 mg, temp=100° C., 2 bar $O_2$, FIG. (10) depicts effect of Pore size of the support and basic metal on the Yield of FDCA Conditions: 1.3 mmol HMF, 20 ml Water, 2% Ru—Mg-OMS-2=80 mg, 100° C., 2 bar $O_2$.

FIG. (11) depicts effect of Recycle study on the yield of FDCA Conditions: 20 ml water, 110° C., 2 bar $O_2$. 4 h. R-1=HMF=0.2210, 2% Ru—Mg-OMS-1=140 mg; R-2=HMF=0.1179, 2% Ru—Mg-OMS-1=80 mg; and R-3=HMF=0.0940, 2% Ru—Mg-OMS-1=60 mg FIG. (12) depicts effect of temperature and reaction time on GA yield
(a) 60° C., (b) 65° C., (c) 70° C., (d) 75° C.
Reaction conditions: 1 mmol glucose, 25 ml water, 4 wt % Au—Mg-OMS-1 (Substrate/metal=50), 2 bar $O_2$ FIG. (13) depicts effect of metal, temperature and reaction time on GA yield
(a) 4 wt % Au—Mg-OMS-1, (b) 2 wt % Au+2 wt % Pt—Mg-OMS-1, (c) 4 wt % Pt—Mg-OMS-1
Reaction conditions: 1 mmol glucose, 25 ml water, substrate/metal=50, temp 65° C., 2 bar $O_2$ FIG. (14) depicts effect of substrate to metal mole ratio on the GA yield
(a) Glucose/Au=25, (b) Glucose/Au=50, (c) Glucose/Au=75, (d) Glucose/Au=100
Reaction conditions: 1 mmol Glucose, 25 ml water, 4 wt % Au—Mg-OMS-1, 65° C., 2 bar $O_2$.

FIG. (15) depicts effect of reaction time on Glyceric acid yield
Reaction conditions: 1 mmol glycerol, 20 ml water, 2 wt % Pt—Mg-OMS-1 (glycerol/Pt molar ratio—150), 60° C., 2 bar $O_2$.

FIG. (16) depicts effect of temperature and reaction time on the FA yield,
(a) 90° C., (b) 100° C., (c) 110° C.
Conditions: 1.3 mmol HMF, 25 ml water, 2% Ru—Mg-OMS-1=100 mg, 2 bar $O_2$.

FIG. (17) depicts effect of substrate to metal ratio on the yield of FA
Substrate to Ru mole ratio: (a) 70, (b) 88, (c) 135, (d) 180
Conditions: 1 mmol HMF, 25 ml water, 2 wt % Ru—Mg-OMS-1=, 2 bar $O_2$.

FIG. (18) depicts effect of Role of Support on the Yield of FA
Conditions: 1.3 mmol furfural, 25 ml water, Mg-OMS-1=100 mg, 100° C., 2 bar $O_2$

ABBREVIATIONS

OMS: Octahedral Molecular Sieve
HMF: 5-Hydroxymethyl Furfural
FDCA: 2,5-furandicarboxylic add

DETAILED DESCRIPTION OF THE INVENTION

The invention will now be described in detail in connection with certain preferred and optional embodiments, so that various aspects thereof may be more fully understood and appreciated.

The invention provides a novel, cost effective, stable and recyclable catalyst composition i.e. A-B-OMS, wherein 'A' is selected from metals; 'B' is selected from alkali or alkaline earth metals; and OMS is octahedral molecular sieve which includes synthetic todorokite (OMS-1) and cryptomelane (OMS-2); and characterization thereof.

The metal (A) is selected from the group consisting of Pt, Pd, Au, Ru, Rh, Ni, Co, Cu and Os or combination thereof in the range of 0.1-5 wt % of catalyst; the alkali or alkaline earth metals (B) are selected from the group consisting Na, Li, K, Rb, Cs, Mg, Ca, Sr, and Ba or combination thereof in the range of 0.1-10 wt % of the catalyst and OMS is manganese oxide octahedral molecular sieve selected from the group consisting of Mg-todorokite (OMS-1) and K-cryptomelane (OMS-2).

The Mg-OMS-1 (Todorkite) is a microporous tunnel structure of manganese oxide. It contains one-dimensional tunnels formed by 3×3 edge and corner shared $MnO_6$ octahedra. Its composition is $Na_{0.014}.Mg_{0.24}0.051MgO.MnO_{1.78}.0.92H_2O$ and the tunnels have dimensions of 6.9×6.9 Å.

The invention provides process for preparation of stable, novel, recyclable catalyst (A-B-OMS) comprising steps of;
a) Oxidizing metal acetates to obtain alkali buserite;
b) ion-exchanging of alkali-buserite with metal (B) salts and subsequent conversion to B-OMs;
c) Loading of the metal (A) on B-OMS in presence of A-metal salts to obtain A-B-OMs.

In the process, the oxidation of acetates takes place in presence of an oxidizing agent selected from the group consisting of $KMnO_4$, peroxides, nitric acid. The metal acetates are particularly Mn and Mg acetates. Further, ion exchange is carried out in presence of B metal salts, particularly Group I and II metal salts of halide, nitrate, sulphate, phosphate such as NaCl, KCl, $MgCl_2$, LiCl, $CaCl_2$, $Mg(NO_3)_2$ and like thereof. The alkali-buserite complex is subsequently heated in the autoclave in the range of 120 to 160° C. for 24-48 h to obtain B-OMS. Further, loading process is performed in presence of (A) metal salts selected from $RuCl_3$, $PtCl_2$, $Pt(NH_3)_4(NO_3)_2$, $RhCl_3$, $Ni(NO_3)_2$, $OsCl_3$, $CuCl_2$, $PdCl_2$, $HAuCl_4$ and stirred at temperature in the range of 60 to 100° C. for 2 to 4 h, followed by treatment with reducing agent such as $NaBH_4$, $LiAlH_4$ filtered and washed.

The instant catalyst composition can be obtained in the form of nanosized structures not limited to nanofibres, nanorods, nanowires, nanoparticle, wherein the fibrous nanorods exhibit clear lattice fringes with the fibre length in the range of 20 to 200 nm in size.

The surface area of B-OMS is increased to the range of 110-130 $m^2 g^{-1}$ after exchanging with 'A', wherein minimum loading of 'A' is carried out in the range of 0.1% to 5% preferably 2% for achieving higher yield of oxidized product and metal B is present in the range of 0.1 to 10 wt % of catalyst. Further the metal A is finely dispersed on the B-OMS i.e. more than 80% i.e. (80%-100%) due to ultra-fine nano particle size of metal 'A' (1.0 nm-2.0 nm).

In accordance with Scheme 2 herein above, the process for synthesis of Ru—Mg-OMS1 alternately called as Ru—Mg-Todorokite catalyst comprises reacting a solution of Mn and Mg acetates to NaOH, to form slurry of manganese and magnesium hydroxides. Subsequently an oxidising agent ($KMnO_4$) is added to the above slurry under vigorous stirring producing corresponding Mg and Mn oxide. Further the MnOx obtained is subjected to aging and stabilized in distilled water to obtain Na Birnessite, which is further stabilized by stirring at room temperature in distilled water to form Na-Buserite salt, followed by ion exchange using $MgCl_2$ by stirring at room temperature to derive Mg-Buserite. Further, the autoclaving in temperature range 140-170° C. results in production of Mg-OMS-1 also referred to as Mg-Todorokite. Finally the loading of $RuCl_3$ to the Mg-Todorokite solution and stirring in the temperature range 60-90° C. for 2-4 h to obtain ruthenium exchanged manganese OMS-1 in high yield. The obtained catalyst has both redox sites (Ru, Mn oxidation) and basic sites (Mg, promoter).

The invention provides a base free green process for selective oxidation of HMF to obtain FDCA in presence of the (A-B-OMS) catalyst composition under optimized condition in shorter time. (cf scheme 3).

Scheme 3: Reaction pathway for the oxidation of HMF to FDCA in presence of A-B-OMS

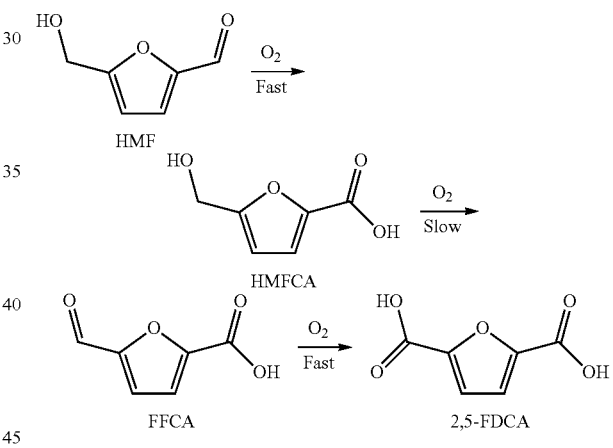

In the invention the base free process comprises the oxidation of HMF to FDCA in the presence of A-B-OMS catalyst at temperature range of 90-120° C. and 1-3 bar oxygen pressure to obtain FDCA with the yield of >95%.

The time required to obtain maximum yield of 90-100 mol % of the product, FDCA is about 4 to 6 h.

Scheme 2: Synthesis of Ru—Mg—OMS-1
Synthesis of Ru—Mg—OMS-1

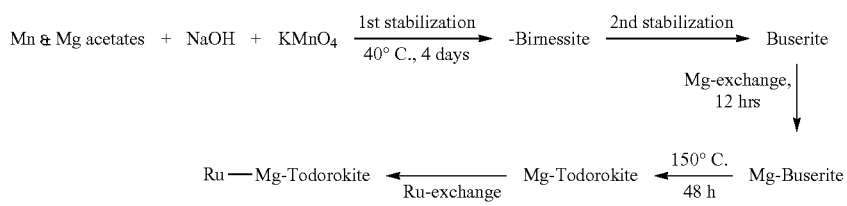

The concentration of HMF is used in the range of 0.5 to 2 mmol, preferably 1 mmol in presence of substantial amount of water.

The base free green process comprises aerobic oxidation of HMF in presence of Ru—Mg-OMS-1. Hydrogen chemisorption results show that Ru was finely dispersed on the catalyst surface. When oxidation of HMF was carried out using $O_2$ at different temperatures, FDCA yield increased with temperature. However, at each reaction temperature, time on stream influenced the yield of FDCA. At 90° C., FDCA yield increased continuously with time reaching a maximum after 8 h on stream. However, at higher reaction temperatures (100 and 110° C.), the maximum yields were reached even at shorter time on stream. The fall in the yield of FDCA after reaching maximum may be attributed to the polymerization of FDCA leading to unwanted products. Initially, HMFCA (5-hydroxymethyl-2-furancarboxylic acid) is formed on oxidation of HMF, which is gradually converted to FDCA, a more stable product. It has to be pointed out that FDCA was practically not formed before all HMF is converted into HMFCA, indicating the slow reactivity of HMFCA compared with HMF. With increase in the catalyst amount, FDCA yield has increased. Ru actively catalyzes the selective oxidation of alcohols (HMF) Magnesium in the OMS-1 lattice appears to be basic enough to reduce molecular oxygen facilitating FDCA formation.

The instant catalyst has both redox (for oxidation) and basic sites (promoter), wherein Ru serves as redox site and Mg as promoter/basic site, thereby oxidation reaction was conducted without addition of any external base, thus making the instant process greener and environment friendly and useful to get very high yield of FDCA in a shorter span of time.

The invention provides the recyclability of the instant catalyst composition which can be used for 3-5 successive runs wherein the catalyst is successfully recycled with only minimal loss in activity and selectivity, as the basic site is part of the structure and does not leach out during the reaction and also obtained very good yields of FDCA within short span of reaction time.

The invention provides characterisation of the instant catalyst/composition by using analytical techniques such as X-Ray diffraction, BET surface area analysis, $H_2$ Chemisorption, thermo gravimetric analysis, SEM and TEM, $CO_2$ temperature programmed desorption and ICP-OES analysis.

Advantageously the present invention does not employ a base in the selective oxidation of HMF to FDCA which makes the above process environmental friendly. Further, the instant invention obviates the leaching of the basic active centre and improves the recyclability of the catalyst. The use of instant catalyst composition makes the oxidation process time saving, cost-effective and industrially viable.

Consequently the present invention provides stable, recyclable A-B-OMS catalyst composition, synthesis and characterization thereof. Further, the invention provides selective base free oxidation of HMF by employing A-B-OMS catalyst to obtain FDCA, wherein the catalyst was highly active for the above oxidations with efficient conversion, selectivity and short reaction time. Further FDCA yield was highly dependent on time, temperature and pressure. Compared with other precious metals, Ru was found to be more active.

Further, the catalysts are stable under the reaction conditions and retain good activity and selectivity for at least upto three successive runs. The catalysts can be useful in selective heterogeneously catalysed oxidation reactions.

EXAMPLES

Following examples are given by way of illustration therefore should not be construed to limit the scope of the invention.

Example 1 a) Catalyst Preparation a. Preparation of Na-Buserite:

A solution of 19.6 g of $Mn(OOCCH_3)_2.4H_2O$ and 3.4 g of $Mg(OOCCH_3)_2.4H_2O$ in 140 mL of distilled deionized water (DDW) was added slowly to a solution of 50 g of NaOH in 160 mL of DDW under vigorous stirring, forming a white slurry of Mn and Mg hydroxides. A solution of 4.8 g of $KMnO_4$ in 140 mL of DDW was added slowly to the slurry under vigorous stirring, producing a brownish black suspension of $MnO_x$. The suspension was aged without stirring at 40° C. for 4 days. Well-crystallized product was filtered out and washed until the pH of the filtrate was below 9.5. The obtained product was further stabilized by stirring at 30° C. for 2 days in distilled water.

b. Ion-Exchange of Na-Buserite and Subsequent Conversion to Mg-Todorokite:

A 200 mL solution of magnesium chloride (0.2 M) was used for ion exchange. The above obtained buserite was ion exchanged to Mg-Buserite by stirring the mixture at 30° C. for 12 h and washed further. A 200 mL solution of magnesium chloride (0.2M) was added to the above solid part and then autoclaved. The autoclaves were heated at 150° C. for 2 days to get Mg-Todorokite. (Mg-OMS-1) (J Luo et al., *Inorg. Chem.* 1999, 38, 6106.)

c. Synthesis of Ru Exchanged Mg-OMS-1:

4 mL of $RuCl_3$ (1 mL contains 5 mg of Ru) was added to 50 mL of water and 1 g of Mg-OMS-1 was added to the above solution and stirred at 80° C. for 3 h. After cooling the above mixture to 30° C., 200 mg of $NaBH_4$ was added and stirred for 1 h, filtered and washed.

Example 2

Synthesis of Ru—Mg—K-OMS-2

1 g of K-OMS-2 was added to a solution containing 100 mL (1M $Mg(NO_3)_2$) and stirred at 80° C. for 6 h followed by washing and drying the solid at 100° C. Then 1 g of the Mg-OMS-2 was exchanged with 20 mg of Ru to get 2% Ru—Mg—K-OMS-2.

Example 3

Catalyst Characterization

Specific surface areas of the catalysts were measured by $N_2$ sorption at liquid $N_2$ temperature, using Quantachrome Autosorb IQ surface area analyzer employing multi point BET method. The catalyst samples were evacuated at 473 K for 3 h at a residual pressure of $2\times10^{-3}$ torr prior to $N_2$ sorption. The isotherms were analyzed in conventional manner in the relative pressure region of p/p0=0.05 to 0.30. $H_2$ Chemisorption study was also conducted using Quantachrome Autosorb IQ. Catalyst was reduced under $H_2$ flow at 250° C. followed by evacuation and chemisorption study was carried at 40° C. Powder XRD measurements of the synthesized and final catalyst powders was carried out using PANalytical powder XRD, XpertPro-1712 equipped with Ni filtered Cu Kα radiation (λ=1.5418 Å), at a scan speed of 1°/min. XRD patterns were collected in the range of 2θ=5-80°.

Transmission electron micrographs (TEM) of the catalysts were recorded on JEOL model 1200EX microscope operating at 100 kVA. Samples were prepared by placing isopropyl alcohol solution of the catalyst on carbon coated grids, followed by evaporation of the solvent at room temperature. Scanning electron micrographs of the samples were recorded using JEOL-JSM-5200 SEM to study the morphology and particle size. The basicity of the catalyst was investigated by temperature-programmed desorption of $NH_3$ ($NH_3$-TPD) using a Micromeritics Autochem-2910 instrument. Prior to TPD run, the sample was activated at 300° C. in He flow (40 mL·min$^{-1}$) for 1 h. Subsequently, the temperature was brought down to 50° C. and $CO_2$ was sorbed by exposing the samples to a stream of 10% $CO_2$ in He (50 mL·min$^{-1}$) for 1.0 h. The temperature was then raised to 100° C. and flushed with He for 1 h at 100° C. to remove the physisorbed $CO_2$. The desorption of $CO_2$ was carried out in He flow (50 mL·min$^{-1}$) by increasing the temperature to 450° C. at 10° C.min$^{-1}$, while monitoring the concentration of $CO_2$ desorbed using a thermal conductivity detector.

Thermal analysis of the samples was performed using a Mettler Toledo TG/DTA instrument in $N_2$ flow (ca. 50 mL min. The samples were heated at a heating rate of 10° C./min in the temperature range 22-800° C., using α-$Al_2O_3$ as reference.

XRD Analysis:

XRD pattern of Mg-OMS-1 clearly shows that all peaks are well resolved and belong to parent Mg-OMS-1. The major peaks are (1 0 0), (0 0 2), (0 0 3) corresponding d-spacing values at 9.8, 4.9 and 3.3 Å$^0$ respectively. XRD peaks of Mg-OMS-1 match with the reported data of Todorokite Mg-OMS-1 structure (JCPDS 13-164). The change in the relative intensity of XRD reflections is of 4.9 and 9.8 Å, which may suggest a gradual transformation from buserite to todorokite (OMS-1). It is clearly observed in FIG. (1) that (a) to (e) is the clear translation of disordered to ordered structure. Ru exchange doesn't lead to the any substantial phase change in OMS-1.

BET Analysis

The specific surface area values for Mg-OMS-1 and 2% Ru—Mg-OMS-1 is depicted in Table 1 herein below. The support Mg-OMS-1 has surface area of 98.7 m$^2$ g$^{-1}$ which increased to 119.8 m$^2$ g$^{-1}$ after exchanging with Ru. The exchanged material has higher external surface area compared to the parent as determined by t-method. This increase in surface area may be due to replacement of exchangeable Mg with larger Ru (undoped) compared to the parent metal oxide. Whereas, the internal surface area of the exchange material has decreased due to the replacement of magnesium by heavier Ru leading to the partial blockage of pores.

TABLE 1

Physiochemical properties of catalysts

| Catalyst | Surface Area (m$^2$/g) |
| --- | --- |
| Mg-OMS-1 | 98.7 |
| Ru—Mg-OMS-1 | 119.8 |

$H_2$ Chemisorption of the Catalyst $H_2$ Chemisorption results clearly demonstrate that Ru was finely dispersed on the catalyst. The size of the crystallite size is found to 1.62 nm.

TABLE 2

H2 Chemisorption results of Ru—Mg-OMS-1

| Analysis gas | Monolayer uptake (μmol/g) | Active metal surface area (m$^2$/g) | Average crystallite size (Å) | Metal Dispersion % |
| --- | --- | --- | --- | --- |
| Hydrogen | 159.8 | 5.9 | 16.2 | 82.9 |

Thermo Gravimetric Analysis

Figure 2:
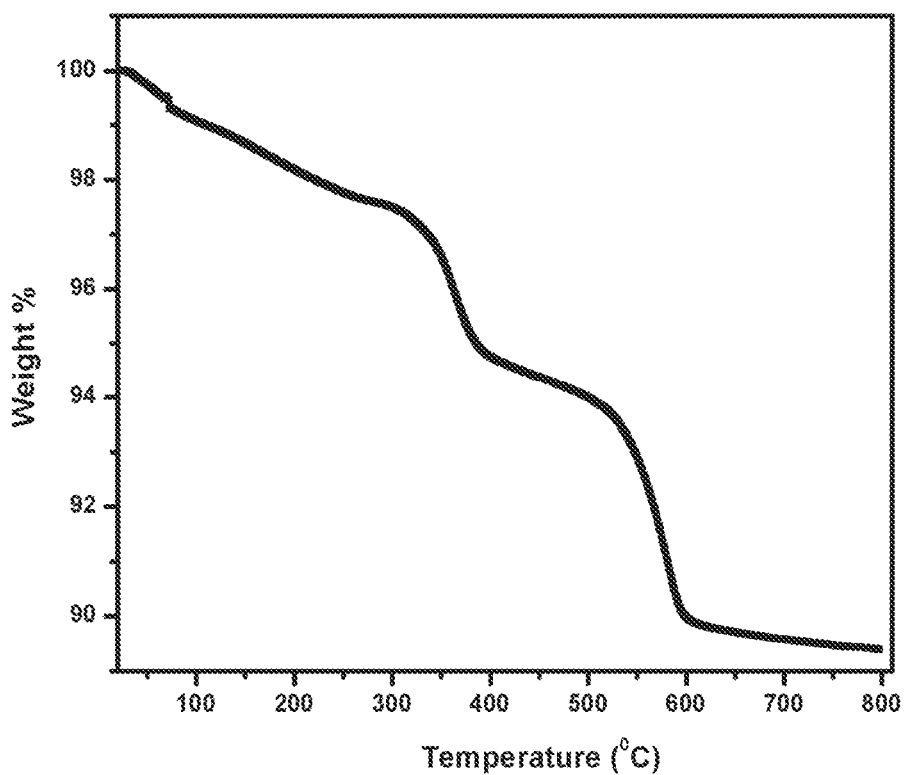
Figure 3:
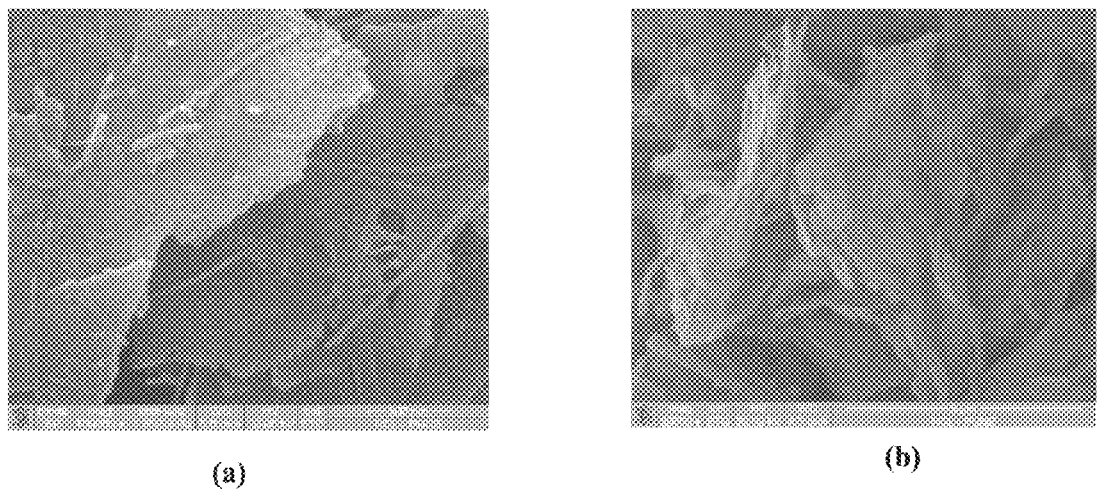
Figure 4:
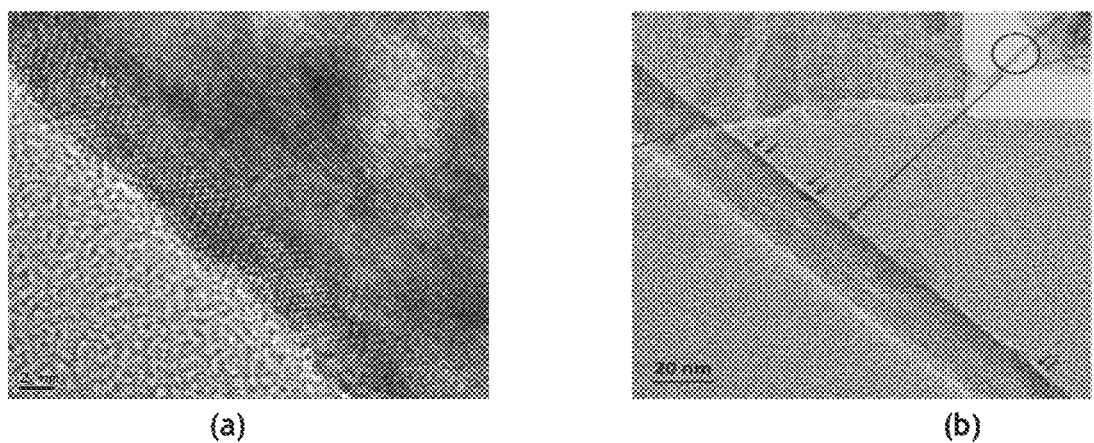
Figure 5:
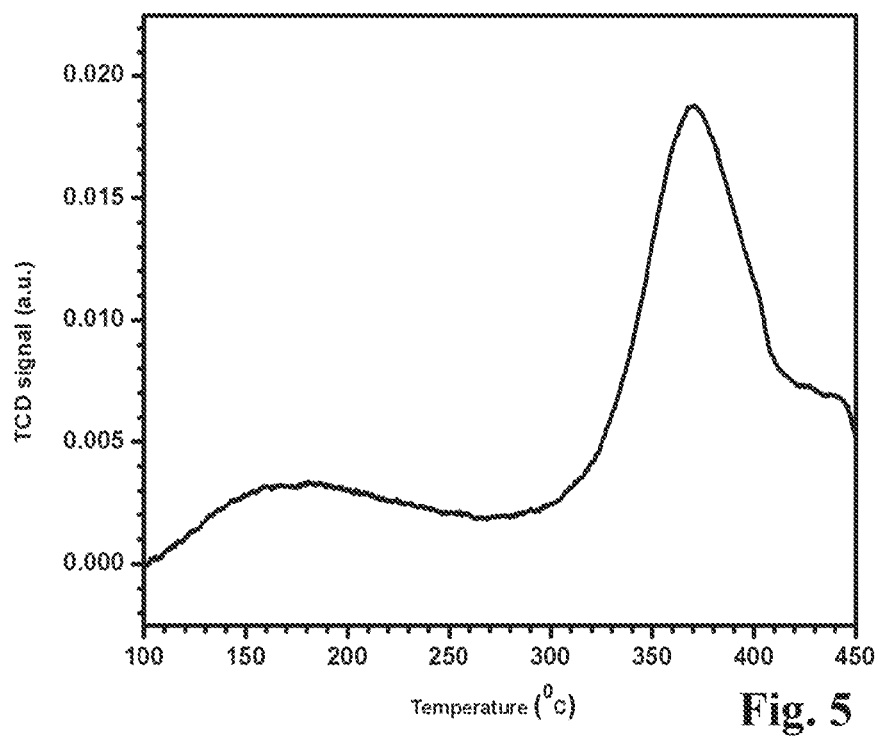
Figure 6:
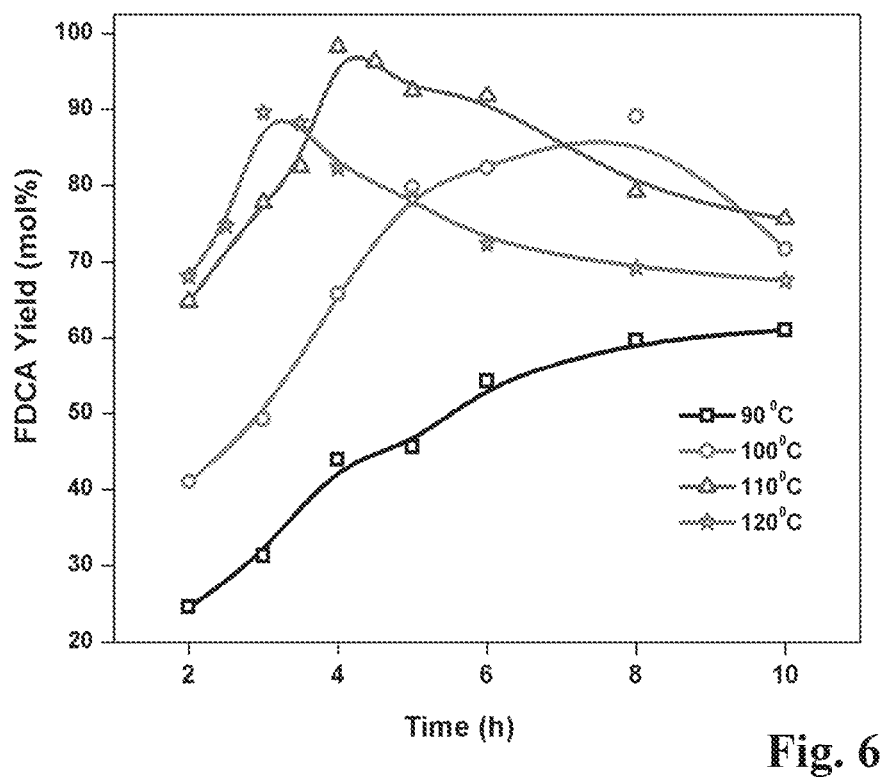
Figure 7:
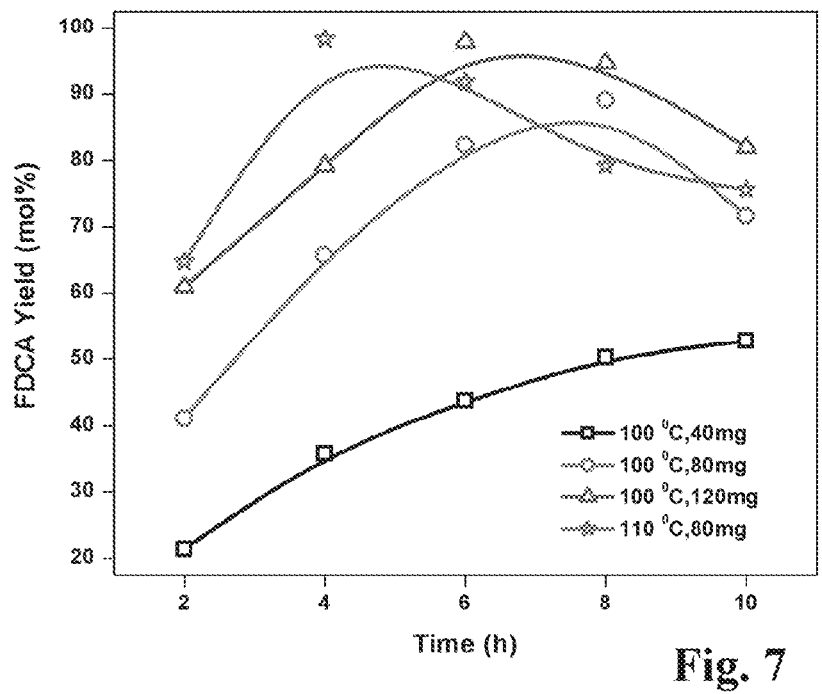
Figure 8:
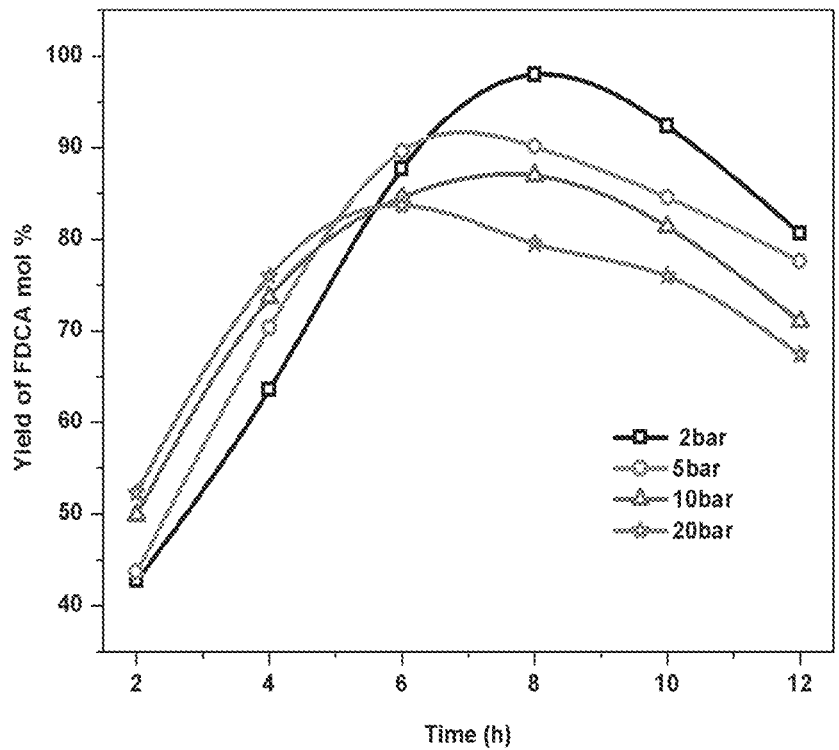
Figure 9:
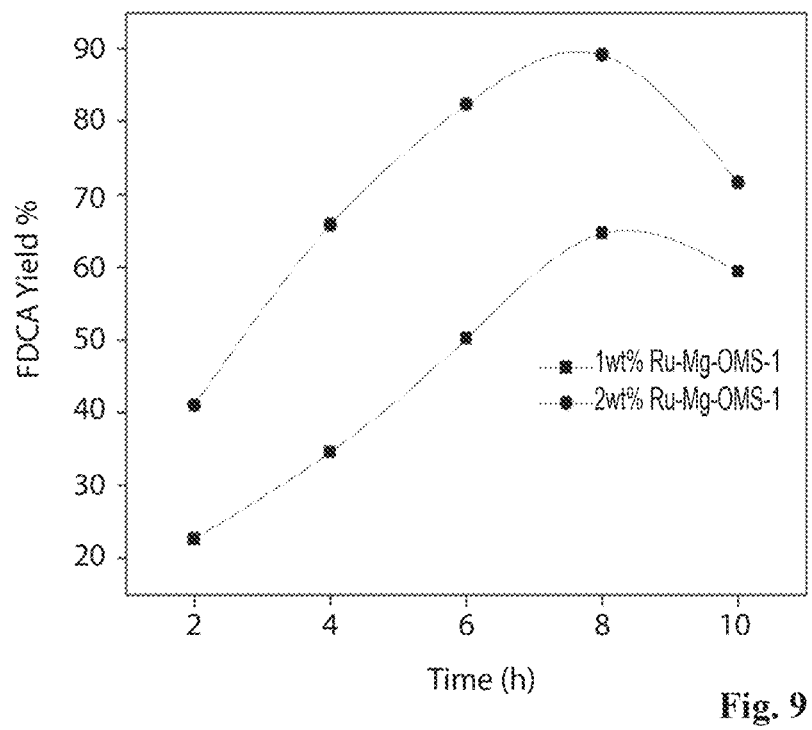

Thermo gravimetric analysis of Mg-OMS-1 was carried out in $N_2$ flow in the temperature range of 22-800° C., while heating the sample at a rate of 10° C./min. The TGA curve of Mg-OMS-1 showed three weight losses in temperature ranges of 50-250° C., 250-400° C., 400-600° C. respectively (FIG. 2). Weight loss below 250° C. was probably due to the loss of water physically adsorbed on the surface. The second weight loss may be mostly attributed to water bound in the tunnel. As the temperature increased, Mn was reduced and oxygen released and then the octahedral framework started to break down and loss of the water bound in the tunnel occurred. The last step of weight loss could be attributed to the great destruction and collapse of tunnel structure, respectively. TGA curve shows that the OMS-1 can stay thermally stable up to 400° C., which is similar to the thermal stability of OMS-1 prepared by other methods (X. H. Feng et al., *Chem. Mater.* 2004, 16, 4330).

SEM and TEM Analysis

The scanning electron micrographs show a fibrous needle and platelet like morphology of Mg-OMS-1 and Ru—Mg-OMS-1 in FIG. (3). The morphology of Mg-OMS-1 is similar to that of Ru—Mg-OMS-1. The result shows that the Ru exchange has no effect on the morphology. TEM images in FIG. (4) shows that the fibrous nanorods with clear lattice fringes and the fibre length are mostly in the range of 20 to 200 nm in size. Similar images were obtained for Ru exchanged material. This indicates that no changes occurred in Todorokite structure upon exchange.

$CO_2$-Temperature Programmed Desorption (TPD)

The $CO_2$-TPD profile in FIG. (5) illustrates that there were two desorption peaks. The first peak begins from 100° C. which centred at 170° C. The second prominent peak starts at 300° C. and centred at 375° C. which was found to be sharp and symmetric. The first peak may arise from the desorption of $CO_2$ from the undoped, weak Mg ions on the surface of the catalyst. The Mg ions which were present in octahedral positions and tunnels give rise the second $CO_2$ desorption peak. The above result substantiates the statement that the magnesium will be majorly in octahedral position.

ICP-OES Analysis

The A-B-OMs catalyst with metal wt % A and B is represented herein below table 3

TABLE 3

ICP-OES Analysis of the catalyst for chemical composition

| Catalyst | Metal wt % | | | |
| --- | --- | --- | --- | --- |
| | Ru | Mn | Mg | K |
| Mg-OMS-1 | — | 44.45 | 3.34 | — |
| Ru—Mg-OMS-1 | 1.98 | 44.13 | 2.51 | — |
| K-OMS-2 | — | 51.33 | — | 3.16 |
| Mg—K-OMS-2 | — | 51.29 | 0.73 | 2.01 |
| Ru—Mg-OMS-2 | 1.79 | 51.32 | 0.96 | 2.48 |

The remaining wt % of the above table majorly constitutes Oxygen.

Example 4

Oxidation of HMF

Reaction was performed in a 50 mL titanium coated Parr reactor. In a typical run, reactor was charged with 1 mmol of reactant, 20 mL of water and 80 mg of catalyst stirred at 110° C. (500 rpm speed). After reaching the desired temperature pure oxygen was sent into the reactor. At the end of reaction, the aqueous samples were filtered using 0.22 μm nylon filter and the filtrate was analyzed using HPLC, equipped with RI detector and Resex ROA-Organic Acid $H^+$ column (300 mm×7.8 mm) with 5 mM $H_2SO_4$ as the mobile phase at a flow rate of 0.6 mL·$min^{-1}$. HMF conversion and FDCA yields were quantified by HPLC through standard calibration curves.

Effect of Temperature and Time on the Yield of FDCA

The effect of temperature and time on HMF oxidation was investigated and results are shown in FIG. (6). During the oxidation of HMF, increasing the temperature from 90-120° C. has a positive influence on the yield of FDCA. At 90° C., yield of FDCA increased continuously with temperature and reaches maximum after 8 hours. However, at higher reaction temperatures (100-120° C.), the yield decreased after reaching maximum at a particular time on stream. This fall in yield was because of the condensation of acid (FDCA) and alcohol (HMFCA), catalyzed by acidic $Mn^{4+}$ ion. Initially, HMFCA (5-hydroxymethyl-2-furancarboxylic acid) was formed on oxidation of HMF, which was gradually converted to FDCA, a more stable product. It has to be pointed out that FDCA was practically not formed before all HMF was converted into HMFCA, indicating the slower reactivity of HMFCA compared with HMF. The time taken to convert HMF to HMFCA was less but the time taken to convert HMFCA to FDCA is higher. Therefore, oxidative conversion of HMFCA to FDCA was found to be the rate determining step for the reaction.

Effect of Catalyst Content on the Yield

The effect of Catalyst content on HMF oxidation was investigated and results are shown in FIG. (7). At 100° C. effect of catalyst amount with TOS was studied. Maximum yield was achieved after 8 h (53.7%) for 40 mg of catalyst, whereas yield was 90.2% after 8 h with 80 mg. For 120 mg of catalyst yield was 97.8% after 6 h. At 110° C., maximum yield (96.6%) was achieved in 4 h, but fell with further increase in time. With increase in catalyst amount, the time taken to achieve maximum yield was minimized due to increase in catalyst content, more active sites were available to drive the reaction for an early completion. From the temp study the inventors had found that increasing temp leads to improved yield of FDCA, so instead of 120 mg of catalyst and increased the reaction temp by 10° C. and achieved the maximum yield of FDCA at 110° C., with 80 mg of the catalyst within 4 hrs of reaction.

Effect of Oxygen Pressure on the Yield:

The effect of Catalyst content on HMF oxidation was investigated and results are shown in FIG. (8). Concentration of oxygen has a marked effect on the yield of FDCA. Oxygen pressure was varied from 2 to 20 bar. HMF conversion was nearly 100% irrespective of oxygen pressure. However, as seen from FIG. (6), FDCA formation was higher (93% at the end of 8 hr) when the pressure was 1 bar than when it was 10 bar (85%) or 20 bar (80%). Higher pressure of oxygen leads to adverse effect on the FDCA yield. An optimum pressure of 2 bar was sufficient to oxidize the intermediates especially the primary alcohol substituent of the furan derivatives.

Effect of Ru Loading:

The effect of metal loading on HMF oxidation was investigated and results are shown in FIG. (9). Metal loading is essential to get high yields of FDCA. As seen from FIG. (9) FDCA yield increases with increasing amount of Ru loading indicated that a minimum loading of 2 wt % Ru which was essential for achieving higher yield of FDCA.

Effect of Different Noble Metals on the Yield of FDCA:

The effect of nobel metal on HMF oxidation was investigated and results are shown in table 4

TABLE 4

Effect of different Nobel metals on FDCA yield

| S. No | Catalyst | FDCA Yield |
|---|---|---|
| 1 | 2% Au—Mg-OMS-1 | 68.25 |
| 2 | 2% Pt—Mg-OMS-1 | 52.36 |
| 3 | 2% Pd—Mg-OMS-1 | 44.22 |

Conditions: 1 mmol HMF, 20 ml Water, 8 h, Catalyst=80 mg, 100° C., 2 bar $O_2$

The above oxidation reaction was conducted with different metals on the same support. From the table, one can see that the yield of FDCA follows the following trend Au>Pt>Pd.

Effect of Pore Size of the Support and Basic Metal on the Yield of FDCA

The Effect of pore size of the support and basic metal on HMF oxidation was investigated and shown in the FIG. (10). The investigated support OMS-1 has pore size of 6.9 $A^0$, which was bigger than the OMS-2 which has pore size of 4.6 $A^0$ belong to same family. In order to find out the role of pore size effect, the inventors had prepared Mg-OMS-2 by exchanging K with Mg.

Figure 10:
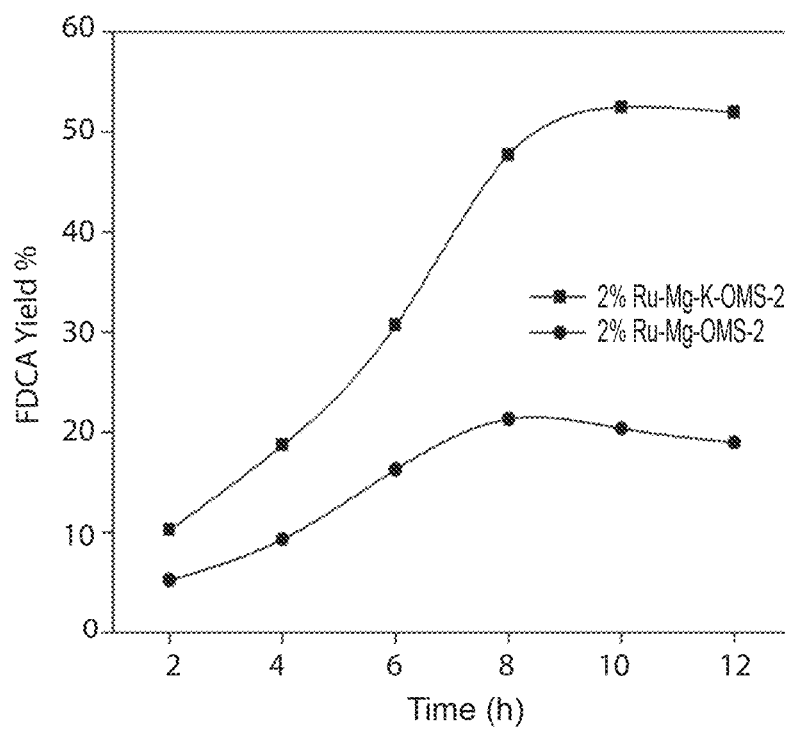
Figure 11:
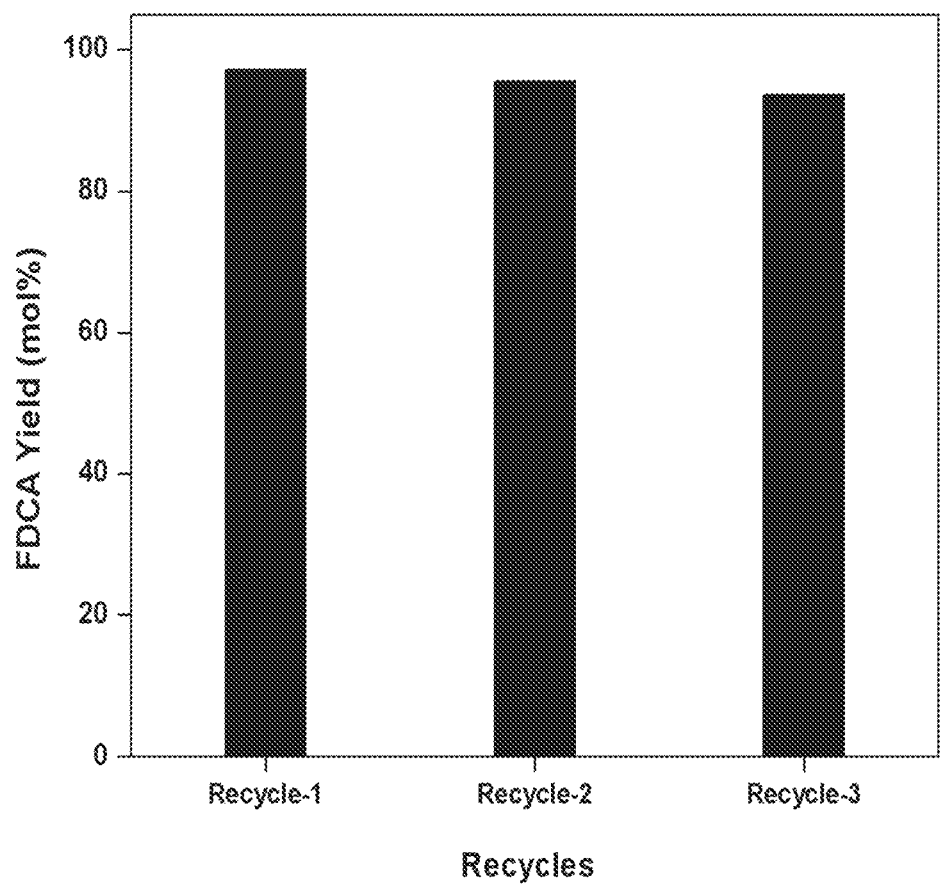

FIG. 10 demonstrates the effect of basic metal on the yield. In order to carry out the investigation the inventors have synthesized Mg exchanged K-OMS-2. Nearly 0.7 wt % of Mg was exchanged in the OMS-2 lattice. With Mg exchange, K content was found to be decreased (from ICP). Compared to the potassium, magnesium exchanged support showed better yield.

FIG. 10 also indicates that the yield of FDCA was much Less compared to the OMS-1 support under same conditions. The decrease in yield may be attributed to the inability of the substrate to enter in to the tunnel to be exposed to the tunnel where Mg and Ru are present.

In order to study the effect of support; parent Mg-OMS-1 was also used as the catalyst. Complete conversion of HMF was obtained but instead of FDCA, formation of HMFCA was observed (Scheme 2). In the catalyst the major percentage of Mn was in +4 oxidation state. Since support has $Mn^{4+}$/$Mn^{3+}$ redox couple (Alexey Serov et al., Appl. Catal. B. Environmental, 2009, 90, 313), it drove the oxidation of much reactive aldehyde group to acid to form HMFCA. While the above redox couple potential was not sufficient to oxidize the much less reactive alcohol group of HMF.

Analysis of Recyclablity of Catalyst

The catalyst was successfully recycled with only minimal loss in activity. Even Ru and Mg contents were retained in the catalyst, showing that the catalyst did not leach out under reaction conditions.

Example-5

Oxidation of glucose to Gluconic Acid

Liquid phase batch reactions were conducted in a 50 ml Parr autoclave. In a typical run, reactor was charged with required amount of reactant, 25 ml of water and catalyst. The reactor was flushed with $O_2$ gas and heated to the desired temperature. After attaining the desired temperature, oxygen was sent in to reactor at desired pressure and flow rate. The aqueous samples after the reaction were filtered using 0.22 μm nylon filter and the filtrate was analyzed using HPLC, equipped with UV detector and Phenomenex Rezex ROA-Organic Acid $H^+$ column (300 mm×7.8 mm). Glucose conversion and yield of Gluconic acid (GA) were quantified by HPLC using standard calibration plots of standard sample.

Effect of Temperature on Gluconic Acid Yield

Figure 12:
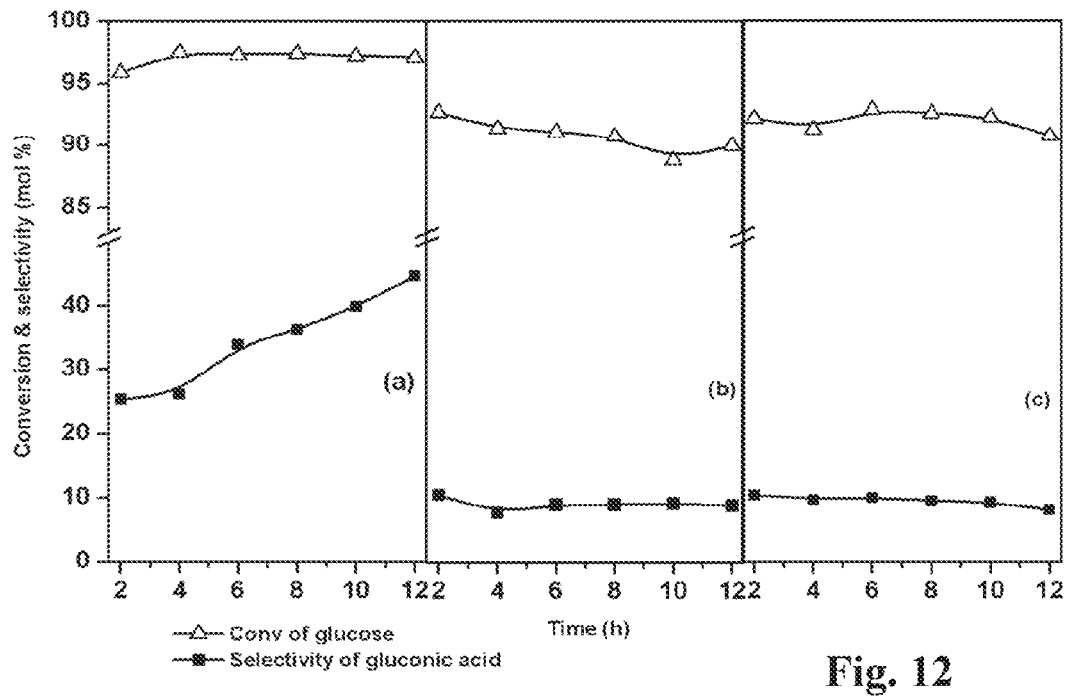

The influence of reaction temperature on D-glucose oxidation was examined and the results are shown in FIG. 12 It is clear that the temperature promotes the conversion of glucose, which has progressively increased from 41.6 to 83.3%, when temperature is raised from 60 to 75° C. The selectivity to GA remains more or less constant in temperature range from 60-70° C., but further increase of temp to 75° C. leads to a gradual reduction in selectivity with increasing time of the reaction. Longer contact time of the product GA with the catalyst at high temperatures (above 70° C.) must be leading to further oxidation. However, the GA selectivity at temp below 75 remains more or less same even at longer contact times. Since, the reaction is base free, pH of the reaction solution was ~7, which prevents Au sintering, maintaining stable activity and product selectivity. From the results, it can be concluded that the reaction temperature of 70° C. is optimum for better selectivity of desired products at reasonably good conversion.

Influence of Precious Metal on Gluconic Acid Yield

Figure 13:
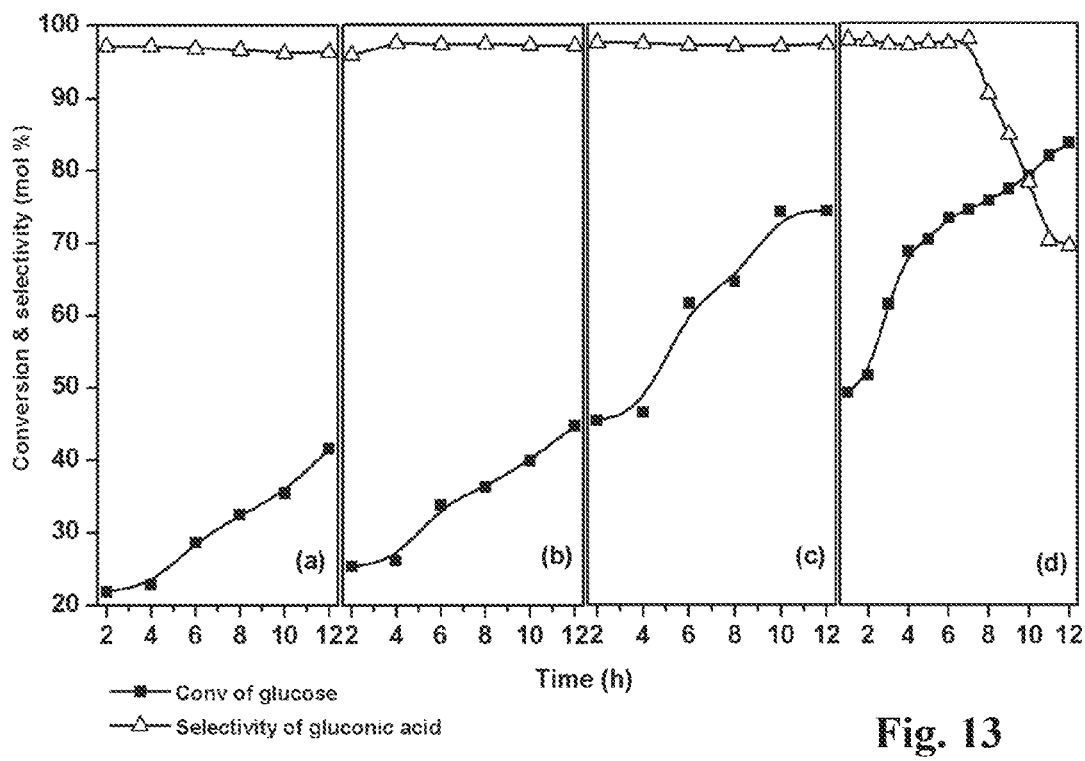

Other precious metals were also studied using OMS-1 as support. These results are shown in FIG. 13. Rate of conversion of glucose is found to be higher in case of Au catalysts and the GA selectivity was >95 mol % throughout the duration of the reaction. When catalyst contain Pt or Pt in combination with Au, the catalyst was not effective. The catalyst did not readily oxidize the aldehyde moiety of glucose chain under these conditions. The present results are in agreement with the literature that Au catalysts are more active in glucose conversion and selective to gluconic acid formation.

Effect of Substrate to Metal Mole Ratio

Figure 14:
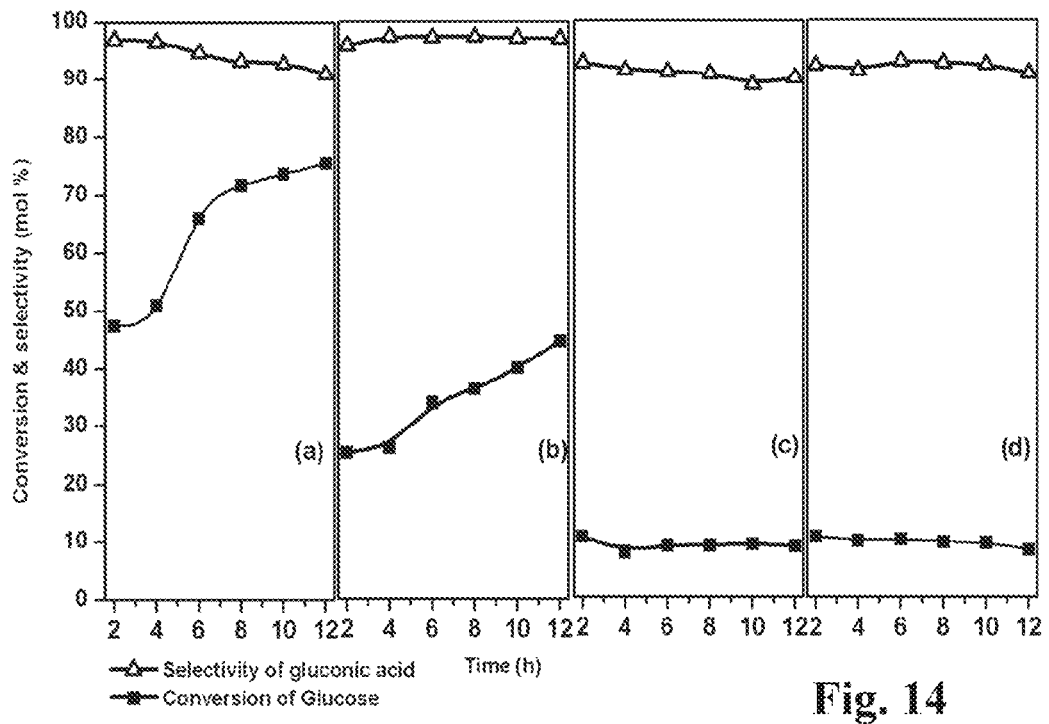

FIG. 14 demonstrates the influence of the substrate to metal ratio on the performance of the catalyst in glucose oxidation. It is evident that the glucose conversion increased from 47 to 75% in 12 h of reaction time, at lower substrate to metal ratios. The yield of GA obtained in this case is approximately 69%. At higher ratios, in addition to conversion, even the selectivity to GA slightly dropped.

Example-6

Base Free Oxidation of Glycerol to Glyceric Acid

Figure 15:
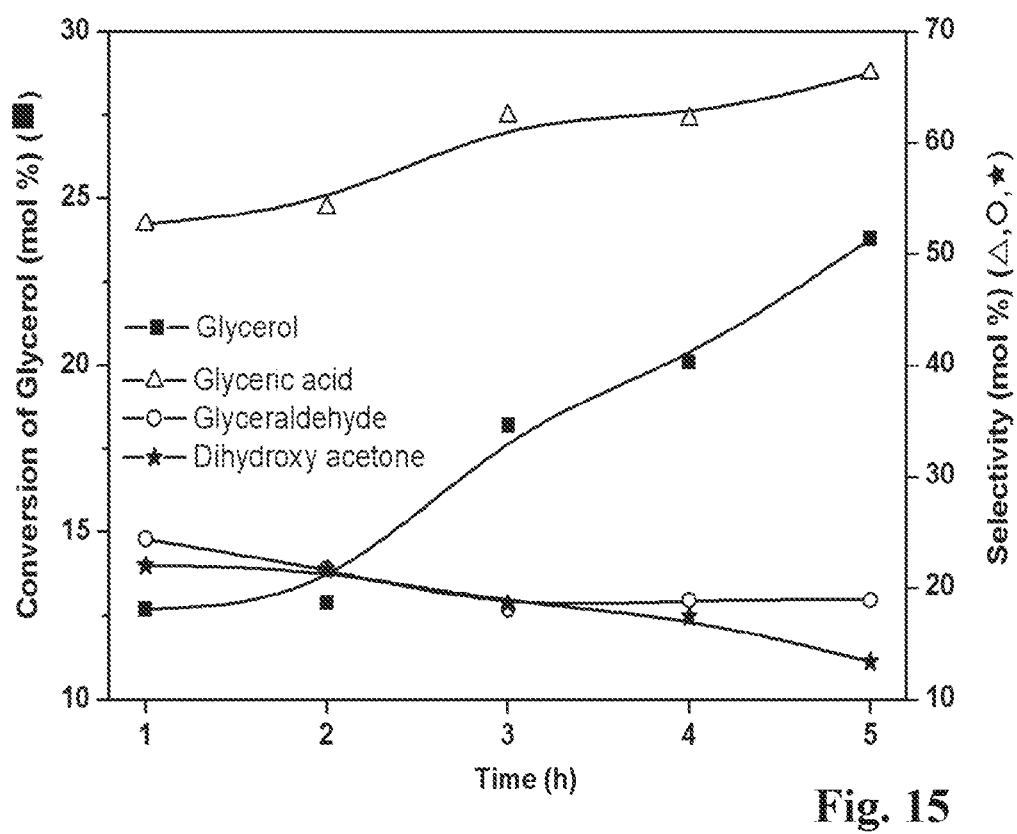

The oxidation of glycerol with dioxygen was also investigated using 2 wt. % Pt—Mg-OMS-1 catalysts and the results are shown in FIG. 15. Conversion of glycerol increased gradually with reaction time. Selectivity of Glyceric acid also increased along with it, while glyceraldehyde and dihydroxy acetone were found to fall with time. This phenomenon can be explained by the reason that glyceraldehyde and its isomer dihydroxy acetone were the initial products of the oxidation and gets oxidized to glyceric acid with Longer contact time with the catalyst. The above results were in accordance with published literature (S. Demirel et al., Appl. Cata., B, 2007, 70, 637).

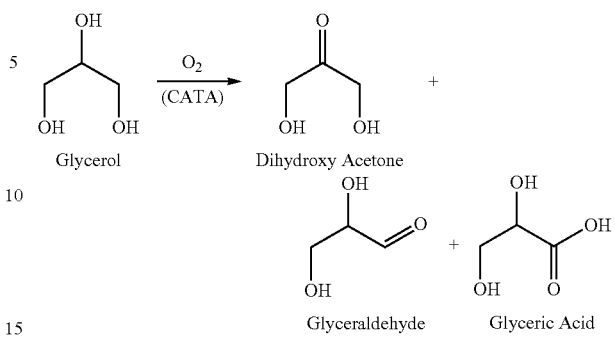

Scheme 4: Selective oxidation of Glycerol to Glyceric Acid

Example-7

Base Free Oxidation of Furfural to Furoic Acid

Reaction was performed in a 50 ml parr autoclave reactor. In a typical run, reactor was charged with 1.3 mmol of reactant, 25 ml of water and 100 mg of catalyst stirred at 600 rpm. On reaching the desired temperature (100° C.), oxygen was sent into the reactor continuously. At the end of reaction, the aqueous samples were filtered using 0.22 μm filter and the filtrate was analyzed using HPLC, equipped with RI detector and Phenomenex Rezex ROA-Organic Acid $H^+$ column (300 mm×7.8 mm). Furfural conversion and furoic acid yield were quantified by HPLC using standard calibration curves of reference compounds.

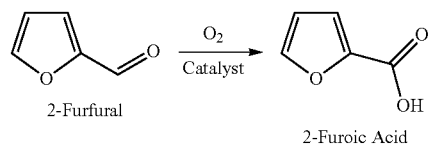

Scheme 5: 2-Furfural oxidation to 2-furoic acid

Effect of Temperature and Reaction Time on the Yield of FA

Figure 16:
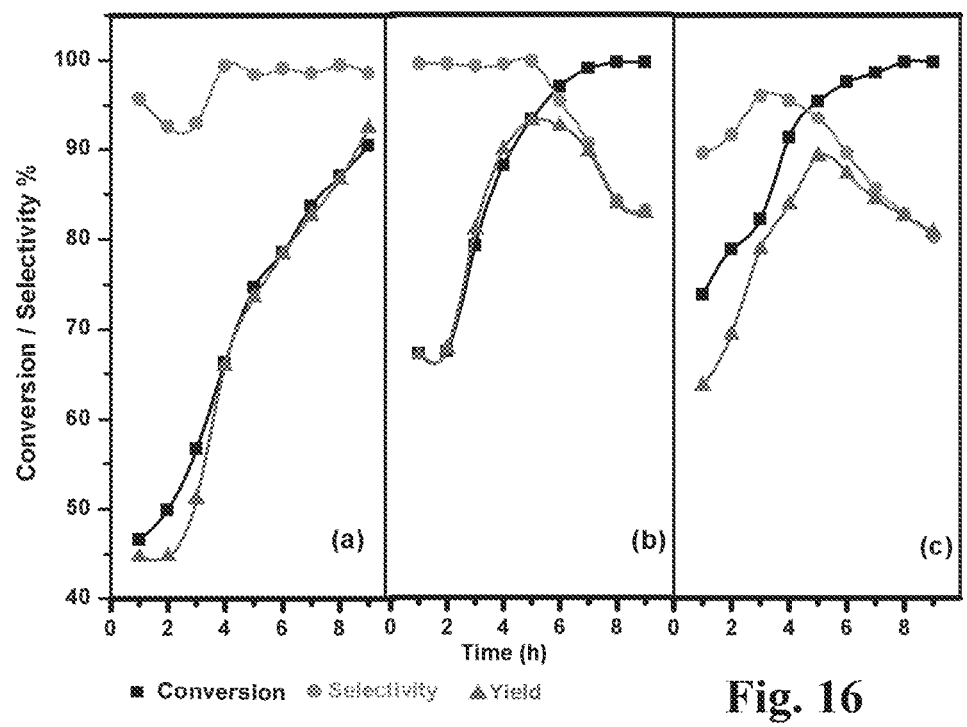

Reaction temperature and time are important parameters that play predominant role in attaining selective product in any oxidation reactions. The effect of temperature and time on furfural oxidation was investigated and results are shown in FIG. 16. Increasing the temperature from 90 to 110° C. leads to enhancement of FA yield. At 90° C., yield of FA increased continuously with reaction time. Increase in temp to 100° C. helps to attain maximum yields faster, but further increase in temperature to 110° C. leads to drop in FA selectivity. This decrease in FA selectivity beyond 100° C. may be attributed to the degradation of furfural through secondary reactions. Hence, maintaining optimum temperature is very important.

Effect of Substrate to Metal Ratio

Figure 17:
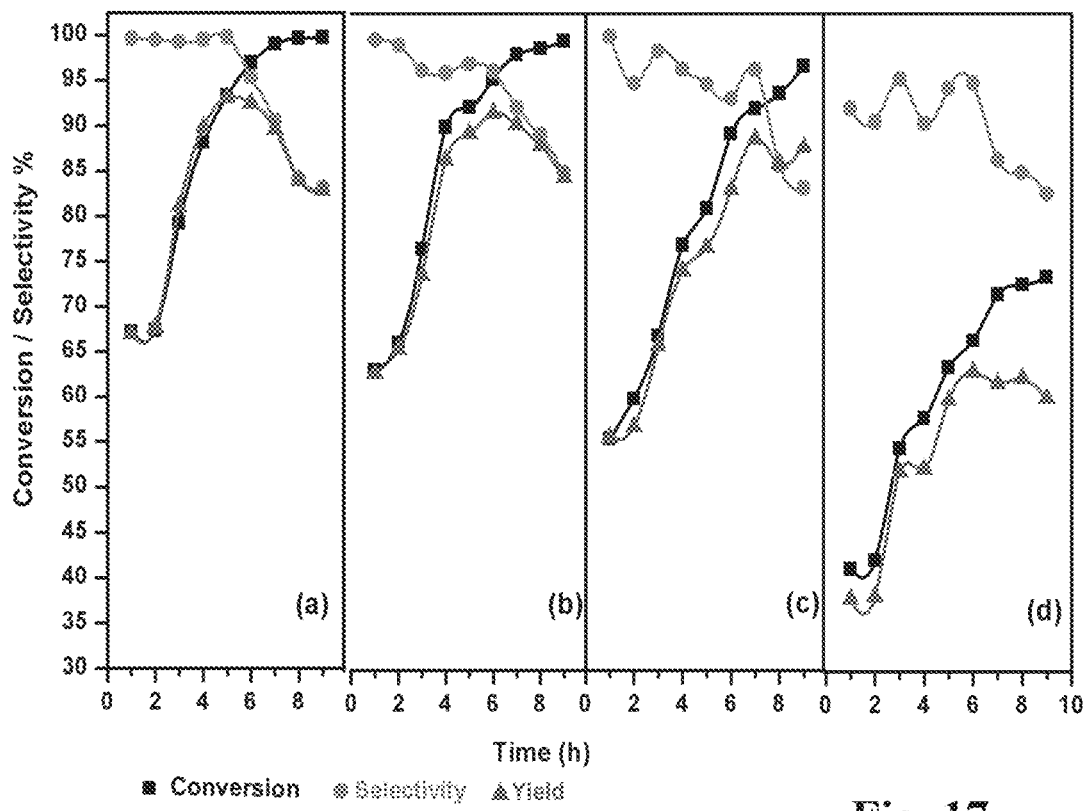

The effect of the substrate to metal ratio on 2-furfural oxidation was studied and found to be extremely important. Rate of conversion of 2-furfural increased at lower substrate to metal mole ratio. Conversion is found to increase with reaction time irrespective of the ratio. But comparatively steep rise in conversion is observed at lower ratios. Rate of formation of FA from furfural is higher at lower substrate to metal ratio. Major issue for this reaction is at higher TOS, the formed FA tends to degrade in to secondary products with higher contact time. So, in order to achieve maximum yield of FA, it is recommended that the reaction must be stopped before the degradation of FA begins. The below (FIG. 17) clearly shows the rote of substrate to metal ratio.

Effect of Precious Metals on FA Synthesis

TABLE 5

Influence of precious metals on the Yield of 2-Furoic Acid

| S. No | Catalyst | Time | Conversion of Furfural (mol %) | Selectivity of 2-Furoic Acid (mol %) |
|---|---|---|---|---|
| 1 | 2 Wt % Ru—Mg-OMS-1 | 6 | 95.2 | 96.0 |
|   |   | 12 | 99.69 | 82.63 |
| 1 | 2 Wt % Au—Mg-OMS-1 | 6 | 17.33 | 74.5 |
|   |   | 12 | 22.1 | 68.4 |
| 2 | 2 Wt % Pt—Mg-OMS-1 | 6 | 49.37 | 60.27 |
|   |   | 12 | 61.74 | 63.7 |
| 3 | Au—Pt(1:1 wt %)Mg-OMS-1 | 6 | 21.7 | 88.0 |
|   |   | 12 | 58.1 | 92.9 |

Conditions: 1.3 mmol furfural, 25 ml water, Substrate: metal mote ration=88, 100° C., 2 bar $O_2$ Effect of different metal on the yield of FA was studied and tabulated in the above table. It was observed that the Ru metal was found to most active among all other precious metals. Bimetallic supported OMS-1 catalyst was found to more selective to FA even though rate of conversion is low.

The increasing order of activity with the precious metals for the oxidation of furfural is as follows

Role of Support as Catalyst

Figure 18:
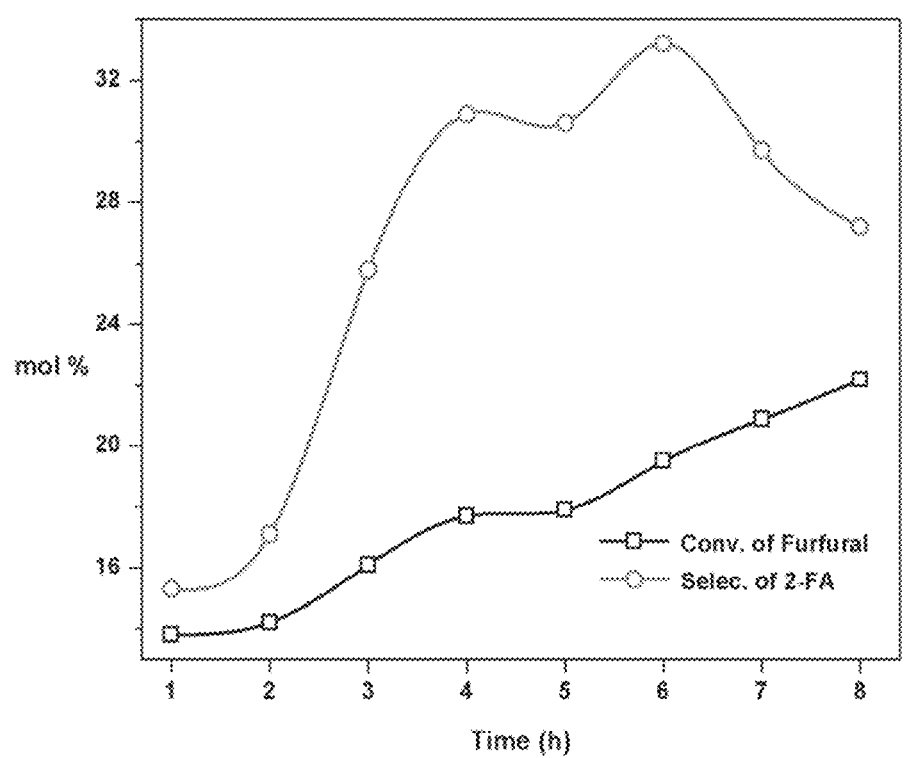

In order to investigate the role of support, reaction was conducted with Mg-OMS-1 catalyst and results were depicted in the fig 18. It was observed that conversion increases with TOS gradually. Selectivity of FA was found to low. The decrease in both Conversion and selectivity's were because of the absence of redox metal. Furfural degrades with TOS and secondary reactions were predominant. So, it is suggested that redox metal is key for the selective oxidation of furfural to 2-Furoic Acid.

Advantages of the Present Invention

Till today, researchers have been using base as a promoter for the oxidation of biomass derived components to chemicals and intermediates. Since usage of base in reaction is corrosive, we need to avoid the usage of base in large scale production. We have developed a catalyst where we have both redox and basic sites for the oxidation of biomass derived components without addition of external base.

Further, the catalysts are stable under the reaction conditions and retain good activity and selectivity for at least upto three successive runs. The catalysts reported here are easy to prepare, the and the process will be a step forward in the direction for potential commercial exploitation of these materials for selective heterogeneously catalyzed oxidation reactions.

We claim:

1. A selective oxidation catalyst having general formula A-B-OMS, wherein
   A is Ru, Au, Pt, Pd, Rh, OS, Ni, Co or Cu either alone or a combination thereof in the range of 0.1-5 wt % of the catalyst;
   B is K, Na, Li, Rb, Cs, Mg, Ca, Sr, or Ba either alone or a combination thereof in the range of 0.1-10 wt % of the catalyst; and
   OMS is an octahedral molecular sieve selected from the group consisting of synthetic todorokite (OMS-1) and K-cryptomelane (OMS-2).

2. The catalyst according to claim 1, wherein the catalyst is selected from the group consisting of Ru—Mg-OMS1, Ru—Mg-OMS2, Ru—Mg—K-OMS1 Ru—Mg—K-OMS2, Au—Mg-OMS1, Pt—Mg-OMS1, Pd—Mg-OMS1 and Au—Pt—Mg-OMS1.

3. A process for the preparation of the catalyst having general formula A-B-OMS according to claim 1, comprising steps of;
   a) ion-exchanging of sodium-buserite with a metal (B) salt by stirring at a temperature ranging between 25-35° C. for a period ranging between 12-36 hrs followed by adding solution of metal (B) salts into it and heating at temperature ranging between 120° to and 160° C. for a period ranging between 24-48 hrs to obtain B-OMS; and
   b) stirring B-OMs as obtained in step (a) with an A-metal salt at a temperature ranging from 60 to 100° C. for 2 to 4 h and after cooling, adding a reducing agent selected from the group consisting of $NaBH_4$ and $LiAlH_4$ into it and stirring at a temperature ranging between 30-40° C. for a period ranging between 1-3 hrs to obtain A-B-OMs.

4. The process according to claim 3, wherein the metal (B) salt used in step (a) is selected from the group consisting of NaCl, KCl, $MgCl_2$, LiCl, $CaCl_2$, and $Mg(NO_3)_2$.

5. The process according to claim 3, wherein the (A) metal salt used in step (b) is selected from the group consisting of $RuCl_3$, $PtCl_2$, $RhCl_3$, $OsCl_3$, $CuCl_2$, $PdCl_2$, and $AuCl_3$.

6. A base free green process for selective oxidation in presence of the catalyst (A-B-OMS) as claimed in claim 1, wherein the process comprises:
   charging a reactant in the range of 0.5 to 5 mmol, water and the A-B-OMS catalyst in a reactor;
   heating the reactor while stirring at a speed ranging between 500-1000 rpm to reach a temperature ranging between 90-120° C.; and
   after reaching the temperature, sending oxygen into the reactor at a pressure ranging between 1-3 bar to obtain an oxidized product.

7. The process according to claim 6, wherein the reactant is selected from the group consisting of 5-hydroxymethylfurfural (HMF), Glucose, Glycerol and Furfural.

8. The process according to claim 6, wherein the oxidized product is selected from the group consisting of 2, 5-furandicarboxylic acid (FDCA), Gluconic Acid, Glyceric acid and 2-Furoic Acid.

9. The process according to claim 6, wherein the A-B-OMS catalyst is selected from the group consisting of Ru—Mg-OMS1, Ru—Mg-OMS2, Ru—Mg—K-OMS1 Ru—Mg—K-OMS2, Au—Mg-OMS1, Pt—Mg-OMS1, Pd—Mg-OMS1 and Au—Pt—Mg-OMS1.

10. The process according to claim 6, wherein the molar ratio of the reactant to the catalyst ranges between 50-500.

11. The process according to claim 6, wherein the oxidation is completed within 4-6 h.

12. The process according to claim 6, wherein the yield of the oxidized product is in the range of 10-95%.

13. The process according to claim 4, wherein the metal (B) salt used in step (a) is $MgCl_2$.

* * * * *